US008389004B2

(12) United States Patent
Taylor et al.

(10) Patent No.: US 8,389,004 B2
(45) Date of Patent: Mar. 5, 2013

(54) PROCESS FOR PRODUCING PROTEIN MICROPARTICLES

(75) Inventors: Janet Taylor, Pretoria (ZA); John Reginald Nuttall Taylor, Pretoria (ZA)

(73) Assignee: University of Pretoria, Pretoria (ZA)

( * ) Notice: Subject to any disclaimer, the term of this patent is extended or adjusted under 35 U.S.C. 154(b) by 0 days.

(21) Appl. No.: 13/122,056

(22) PCT Filed: Oct. 7, 2009

(86) PCT No.: PCT/IB2009/054386
§ 371 (c)(1),
(2), (4) Date: Jul. 29, 2011

(87) PCT Pub. No.: WO2010/041203
PCT Pub. Date: Apr. 15, 2010

(65) Prior Publication Data
US 2012/0128779 A1 May 24, 2012

(30) Foreign Application Priority Data
Oct. 7, 2008 (ZA) .................................. 2008/08528

(51) Int. Cl.
*A61K 9/00* (2006.01)
*A61K 9/54* (2006.01)

(52) U.S. Cl. ........................................ 424/458; 424/400

(58) Field of Classification Search .................... 426/89, 426/93, 656, 626; 424/458, 400
See application file for complete search history.

(56) References Cited

U.S. PATENT DOCUMENTS

| 4,650,856 A | 3/1987 | Yagi et al. |
| 5,145,702 A | 9/1992 | Stark et al. |
| 5,705,207 A | 1/1998 | Cook et al. |
| 5,750,183 A | 5/1998 | Yamamoto et al. |

FOREIGN PATENT DOCUMENTS

| WO | WO 91/06286 | 5/1991 |
| WO | WO9610992 | * 4/1996 |

OTHER PUBLICATIONS

Taylor, J. et al., "Formation of kafirin microparticles by phase separation from an organic acid and their characterisation", Journal of Cereal Science, vol. 50, May 2009, pp. 99-105 (XP002568173).
Hurtado-Lopez, P. & Murdan, S. "Zein microspheres as drug/antigen carriers: A study of their degradation and erosion, in the presence and absence of enzymes", Journal of Microencapsulation, vol. 23, No. 3, May 2006, pp. 303-314 (XP002568174).
Taylor et al., "Formation of kafirin microparticles by phase separation from an organic acid and their characterisation", Journal of Ceral Science 50 (2009) pp. 99-105.

* cited by examiner

*Primary Examiner* — Maryam Monshipouri
(74) *Attorney, Agent, or Firm* — Nixon Peabody LLP; Jeffrey L. Costellia

(57) ABSTRACT

The present invention relates to a process for producing protein microparticles in dilute organic acid solutions and in the absence of an alcohol such as ethanol. The microparticles are formed by dissolving a cereal prolamin protein in a concentrated organic acid solution with agitation and then diluting the solution with an aqueous solution. Protein microparticles having vacuoles are thus formed. The protein microparticles may be used to form powders, films, coatings, matrices, scaffolds and the like. Complete films can be formed from the protein microparticles of the invention.

15 Claims, 6 Drawing Sheets

PROCESS FOR PRODUCING PROTEIN MICROPARTICLES

CROSS-REFERENCE TO RELATED APPLICATIONS

This application is the national phase entry of international patent application No. PCT/IB2009/054386 filed Oct. 7, 2009, which claims priority to ZA application No. 2008/08528 filed Oct. 7, 2008. The disclosure of said applications is hereby incorporated herein by reference.

BACKGROUND OF THE INVENTION

The invention provides a process for producing protein microparticles that can be used for micro-encapsulation, matrix or scaffold formation or formed into films or coatings.

A number of processes are known for making microspheres or microparticles from proteins for a variety of applications, such as food coatings, drug delivery and delayed release of pesticides, fertilizers and agents for environmental cleanup. However, non acidic organic solvents such as ethanol or acetone are often used to dissolve the protein. These solvents are often incompatible with and difficult to remove from food, and there has therefore been a reluctance by the food and pharmaceutical industries to use protein film or microparticle systems. Moreover, the use of non acidic organic solvents poses safety issues with the emission of vapours, the fire hazard that they pose, and the possible residuals that they may leave in the food or pharmaceuticals. Many processes also require the use of elevated temperatures.

U.S. Pat. No. 5,736,178 teaches that film forming colloidal dispersions can be made from dilute aqueous acid solutions of gluten-derived protein by causing the protein to precipitate as microparticles. However, the protein has first to be dissolved in an alcohol such as ethanol, which leads to the disadvantages listed above.

The applicant has therefore identified a need for a process for producing protein microparticles in the absence of non acidic organic solvents such as ethanol.

SUMMARY OF THE INVENTION

According to a first aspect of the invention, there is provided a process for making protein microparticles, the process including the steps of:

(a) dissolving cereal prolamin protein in an organic acid with agitation and in the absence of an alcohol; and (b) diluting the solution containing the protein with an aqueous solution and thereby forming protein microparticles having vacuoles.

The protein may be any cereal prolamin protein, such as wheat gluten, barley hordein, maize zein or sorghum kafirin.

The organic acid may be propionic, lactic or acetic acid, or any other suitable acid.

An additive, such as a plasticizer, colouring agent, flavouring agent, preservative, trace mineral, nutrient, enzyme, hormone, nutraceutical probiotic, prebiotic, drug or any combination thereof, may be added to either of steps (a) or (b).

In step (a) the solution of the protein is preferably saturated or highly concentrated.

In step (a), the dissolution is carried out with agitation so as to ensure that the protein microparticles formed have vacuoles. The agitation may be provided by stirring, shaking, homogenisation, bubbling gas through the solution or the like.

In step (b), the solution containing the protein preferably is diluted with water to a final concentration of 2 parts by weight of the protein to 2 to 30 parts by weight of the organic acid to 96 to 68 parts by weight of water, thereby forming the protein microparticles.

The process may be carried out at a temperature of from about 20° C. to 40° C., and more particularly, at room temperature.

The protein may be modified, either physically, chemically or enzymically, prior to or after dissolution, to enhance or alter the functional properties of the microparticles or products such as films formed therefrom. For example, the protein may be crosslinked with tannins or enzymes and/or heated.

The protein microparticles so produced may be used to make films, coatings or matrices as described below.

According to a second aspect of the invention, there is provided a process for making a complete film or coating from the protein microparticles produced as described above, comprising the steps of:

(i) preparing a suspension of the protein microparticles in an aqueous solution of an organic acid to a final concentration of 2 parts by weight of the protein to 2 to 60 parts by weight of an organic acid to 96 to 38 parts by weight of water; and (ii) drying that suspension to form the film or coating.

The film or coating may be clear or cloudy and transparent or translucent.

According to a third aspect of the invention, there is provided a process for making a matrix from the protein microparticles, comprising the steps of:

(i) preparing a suspension of the protein microparticles in an aqueous solution of an organic acid to a final concentration of 2 parts by weight of the protein to 2 to 60 parts by weight of an organic acid to 96 to 38 parts by weight of water;

(ii) washing away the organic acid; and (iii) drying the suspension to form the matrix.

The processes which form the second and third aspects of the invention are preferably carried out in the absence of any non acidic organic solvents, in particular alcohols such as ethanol.

The organic acid may be propionic or acetic acid for the making of films or coatings, or propionic, lactic or acetic acid for the making of matrices, or any other suitable acid.

The final concentration of the suspension may be 2 parts by weight of the protein to 10 to 60 parts by weight of the organic acid to 88 to 38 parts by weight of water.

When the organic acid used is acetic acid, the final concentration is preferably 2 parts by weight of the protein to 20 to 60 parts by weight of acetic acid to 78 to 38 parts by weight of water, more preferably 2 parts by weight of the protein to 20 to 30 parts by weight of acetic acid to 78 to 68 parts by weight of water, most preferably 2 parts by weight of the protein to 21.6 parts by weight of acetic acid to 76.4 parts by weight of water.

However, when the organic acid is acetic acid and the protein is in solution having been extracted from brewers spent grain or other co-products of alcohol production from cereals, then the ratio of protein to acid to water is preferably 2 parts protein to 2 parts acetic acid to 96 parts of water.

When the organic acid used is propionic acid or lactic acid, the final concentration is preferably 2 parts by weight of the protein to 10 to 30 parts by weight of propionic acid or lactic acid to 88 to 68 parts by weight of water, more preferably 2 parts by weight of the protein to 10 to 15 parts by weight of propionic acid or lactic acid to 88 to 83 parts by weight of water, most preferably 2 parts by weight of protein to 10.8 parts by weight of propionic acid or lactic acid to 87.2 parts by weight of water.

In the processes of the second and third aspects of the invention, the suspension prepared in step (i) is preferably allowed to stand for 8 to 24 hours prior to step (ii).

Further, before step (ii), there is preferably added to the suspension a plasticizer in an amount of 0.2 to 0.6 parts by weight of the plasticizer to 1 part by weight of the protein, more preferably about 0.4 parts by weight of the plasticizer to 1 part by weight of the protein.

Examples of plasticizers include glycerol, polyethylene glycol, polypropylene glycol and lactic acid used alone or in combination, dibutyl tartrate, monoglycerides such as oleic acid, palmitic acid or stearic acid, triethylene glycerol and sorbitol, or any other suitable plasticizer or combination thereof.

A preferred plasticizer is a mixture of 1:1:1 (w/w) glycerol: polyethylene glycol (400): lactic acid.

Other additives such as colouring agents, flavouring agents, preservatives, trace minerals, nutrients, enzymes, hormones, nutraceuticals, pharmaceuticals, probiotics, prebiotics, drugs and combinations may be added before step (ii) or (iii).

For the preparation of a film, the suspension of step (i) may be cast directly onto a casting surface. Thereafter the liquid phase is removed by drying, either with or without the application of heat, to give a complete film. The film may be clear or cloudy, transparent or translucent.

For the preparation of a coating on a substrate, the suspension of step (i) may be used to cover a surface of the substrate. Thereafter the liquid phase is removed by drying, either with or without the application of heat, to give a complete coating on the substrate. The coating may be clear or cloudy, transparent or translucent.

For the preparation of a matrix incorporating a compound or substance, the suspension of step (i) has added to it the compound or substance. Thereafter the liquid phase is removed by drying, either with or without the application of heat, to give an opaque matrix encapsulating or incorporating the compound or substance.

According to a fourth aspect of the invention, the protein microparticles may be formed according to the process of the first aspect of the invention so as to incorporate or encapsulate a compound, such as a nutrient, vitamin, enzyme, hormone, pharmaceutical, plasticizer, preservative, colouring agent, flavouring agent, trace mineral, nutraceutical, probiotic or prebiotic, or combinations thereof. The compound may be added to either of the concentrated acid solution or the aqueous solution prior to the formation of the microparticles.

Alternatively, the solution or dispersion containing the protein microparticles may be dried to form a powder.

In this case, according to a fifth aspect of the invention, there is provided a process of making a coating on a substrate from the dried protein microparticles, including the steps of:
(i) mixing the dried protein microparticles with a dry substrate to be coated;
(ii) adding an amount of a concentrated organic acid to the mixture of step (i) so that the protein microparticles coat the substrate; and
(iii) removing the organic acid to fuse the protein microparticles to the substrate to form the coating.

The organic acid may be removed by evaporation, optionally with the aid of heat.

According to a sixth aspect of the invention, there is provided a process of incorporating a compound into a matrix formed from the protein microparticles including the steps of:

(i) mixing the dried protein microparticles with a solution of the compound to be incorporated, the dried protein microparticles being substantially insoluble in the solution; and
(ii) removing the solvent, leaving the compound incorporated into the matrix.

The solvent may be removed by evaporation, optionally with the aid of heat.

According to a seventh aspect of the invention, there is provided a protein microparticle formed from the first process described above. The microparticle must have vacuoles and thus a large internal surface area, and may be softer than a microparticle formed using a non acidic organic solvent, such as ethanol.

According to an eighth aspect of the invention, there is provided an aqueous solution or dispersion of microparticles produced by the first process described above.

According to a ninth aspect of the invention, there is provided a dry powder of protein microparticles produced by the first process described above.

According to a tenth aspect of the invention, there is provided a film cast from a dispersion of microparticles produced by the second process described above.

According to a eleventh aspect of the invention, there is provided a substrate having a coating of microparticles produced by the second or fifth process described above.

The substrate may be selected from the group consisting of foodstuff, fruits, vegetables, minimally processed and processed fruits and vegetables, seeds, nuts, animal feed products, colouring agents, flavouring agents, trace minerals, nutrients, enzymes, hormones, pharmaceuticals nutraceuticals, probiotics, prebiotics, drugs and other pharmaceutical products, medical devices and the like, and combinations thereof.

The starting protein may be a commercially available protein such as commercial zein.

Alternatively the protein can be provided by extracting protein from whole grain (sorghum, maize, wheat, barley, etc. or mixtures thereof) or a co-product such as flour, bran, spent grain, distiller's dry grain with solubles or other co-products of alcohol production from cereals, with an organic acid such as glacial acetic acid, lactic acid or propionic acid, and removing the residual solid material. Mixtures of proteins can also be used for extraction such as those found in brewers spent grain, distiller's dry grain with solubles or other co-products of alcohol production from cereals, which may be mixtures of, but not to the exclusion of other cereal combinations, for example, sorghum and maize in various proportions or barley and maize.

This protein solution can then be used directly in step (b) of the process of the first aspect of the invention.

DETAILED DESCRIPTION

Figure 1:
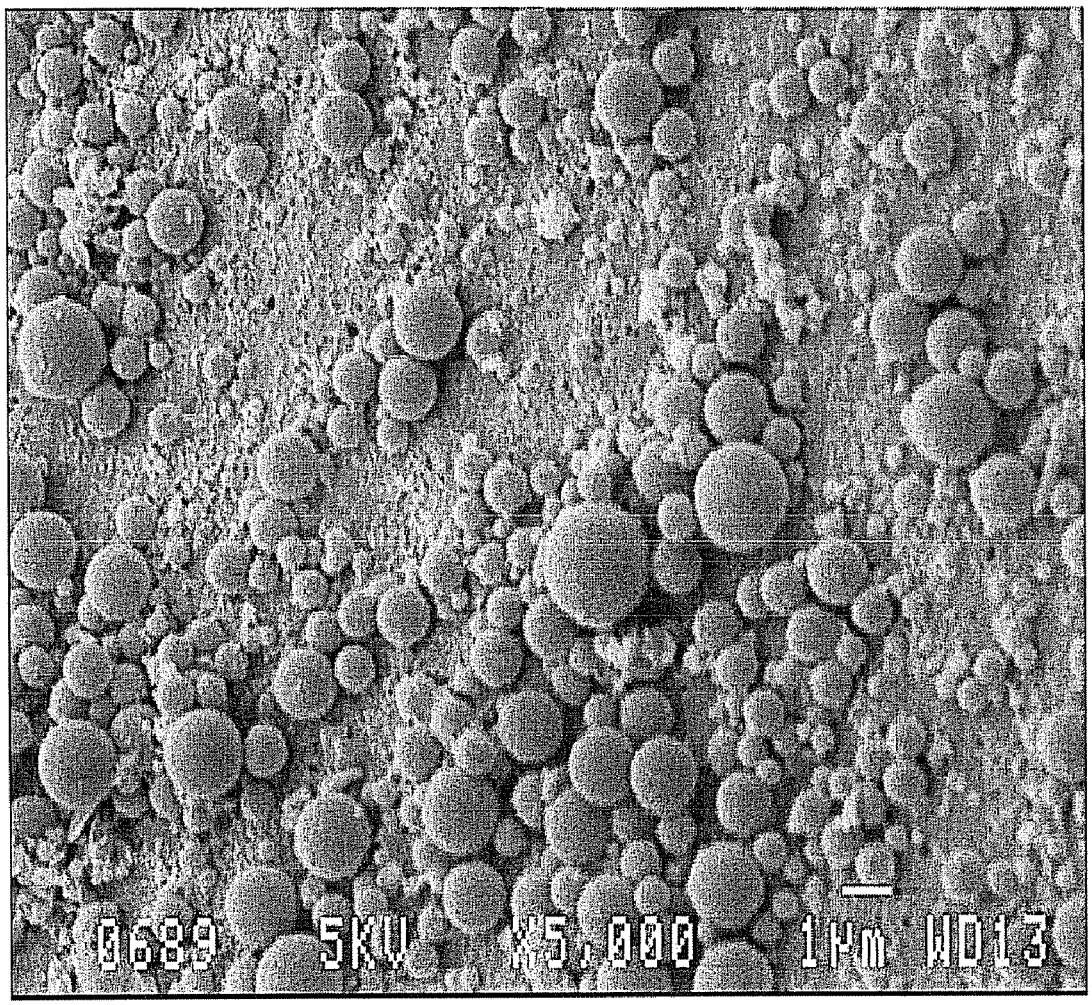
FIG. 1 shows a Scanning Electron Micrograph of kafirin microparticles produced by the prior art method of Parris, Cook and Hicks (2005) J Agric Food Chem 53: 4788-4792, using aqueous ethanol to dissolve the kafirin prior to microparticle formation.

The present invention relates, in a first aspect, to a process for producing dispersions of protein microparticles in dilute organic acid solutions. The microparticles are formed by dissolving the protein in a concentrated organic acid solution and then diluting the solution with an aqueous phase.

The formation of the microparticles is dependant on the relative solubility of the protein in the organic acid solution. As the organic acid concentration is reduced by the addition of an aqueous phase, the protein is no longer soluble and therefore comes out of solution, forming microparticles. A compound may be added to the solution prior to the formation of the microparticles so as to be incorporated into, or encapsulated by, the microparticles. The dispersion of microparticles in dilute organic acid is stable and homogeneous under ambient storage conditions without microbial contamination. The microparticles can be separated from the dilute organic acid, washed and dried to form a powder, or may be used to form a continuous film or to coat a substrate.

As used herein, a concentrated acid is generally regarded as having a concentration of 80% acid or greater, and a dilute acid is generally regarded as having a concentration of less than 80% acid.

No alcohol, such as ethanol, is used in the process and all the constituents can be food compatible, rendering the microparticles suitable for consumption by humans and animals. Unlike known processes for forming microparticles, the present process does not require elevated temperatures, and can be performed at temperatures ranging from 20° C. to 40° C., such as at room temperature. Toxic chemicals are also not required.

Particle size and definition. As used herein, 'micro' refers to a particle with a diameter ranging from nanometers to micrometers. Microspheres are usually considered to be spherical particles, whereas microparticles are usually slightly larger and irregular or non-spherical in shape. In the present invention, the microparticles may be either spherical or of irregular shape, but both will be referred to as microparticles. The term 'microparticle' is therefore intended to be inclusive of microspheres.

The size of the microparticles can range from nano sized (nanometers) to micrometers but more particularly are between 1-10 microns for spherical particles and can be somewhat larger for irregular shaped particles or microparticle aggregates, which may be up to several millimeters. The size can, however, be manipulated to produce larger or smaller particles, depending on the method of preparation, e.g. variation of rate of dilution or shear applied during preparation.

The formation of microparticles with a range of sizes allows for multiple applications. This includes food uses, e.g. film formation for food packaging, edible coatings for the prolongation of shelf-life of food products, and encapsulation of, for example, foodstuffs, animal feed products, food ingredients, enzymes, hormones, colouring agents, flavouring agents, trace minerals, nutrients, pharmaceuticals, nutraceuticals, probiotics, and prebiotics. Other non-food uses could include drug delivery, other medical uses such as tissue engineering, tissue matrixes or scaffolds and coatings for cardiovascular and other biomedical devices, biological semi-conductors and delayed release of pesticides and fertilizers.

Figure 2:
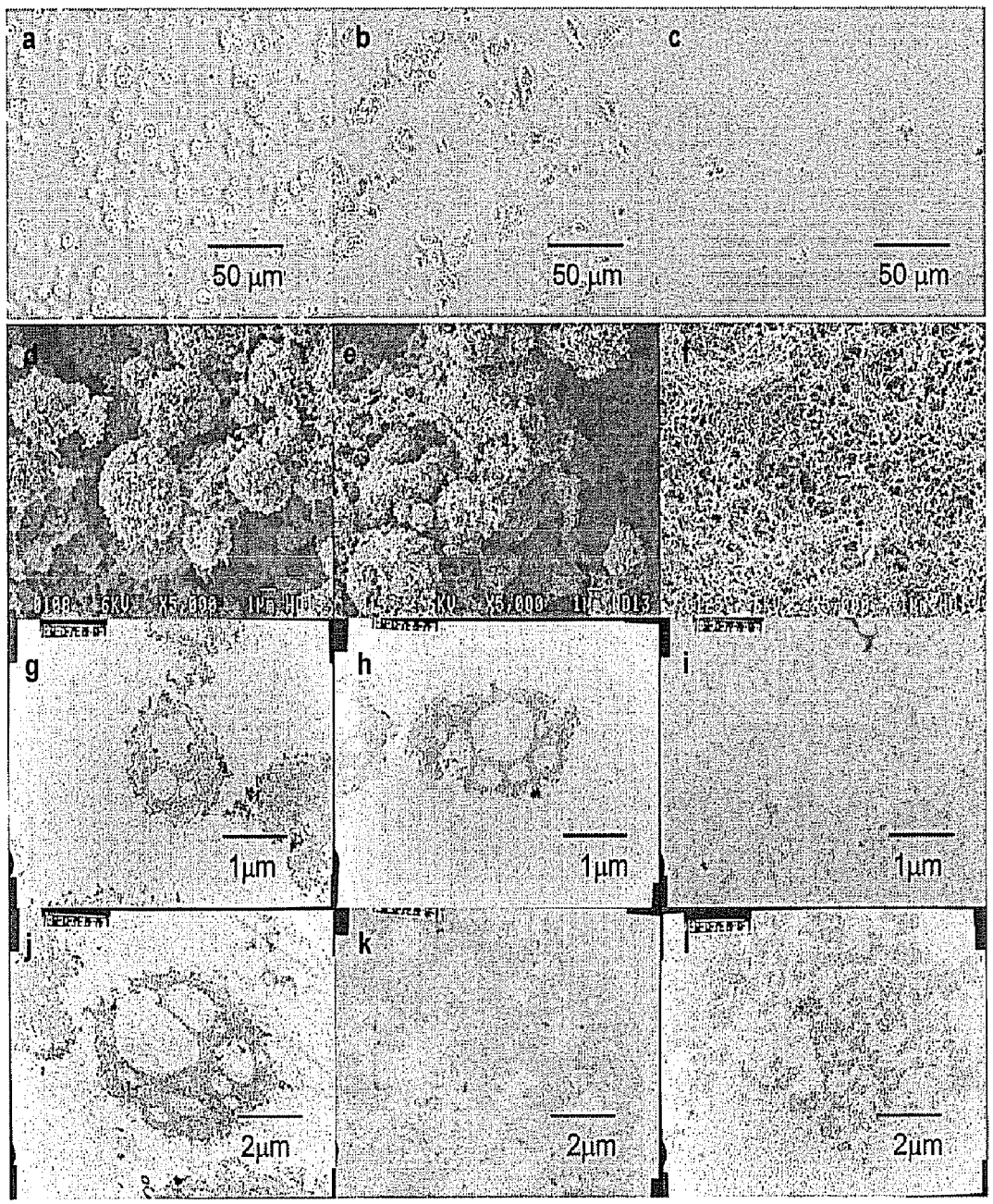
FIG. 2 shows micrographs of kafirin microparticles produced according to the process of the present invention, at different acid concentrations: a-c Light Micrographs at 5.4%, 21.6% and 40% acetic acid, respectively; d-f Scanning Electron Micrograph at 5.4%, 21.6% and 40% acetic acid, respectively; g-i Transmission Electron Micrographs at 5.4%, 21.6% and 40% acetic acid, respectively; j-l Transmission Electron Micrographs higher magnification 5.4%, 21.6% and 40% acetic acid, respectively.

The microparticles made by the process of this invention have a rough porous surface and numerous internal holes or vacuoles as shown by Scanning Electron Microscopy (outer surface) and Transmission Electron Microscopy (internal structure) (FIG. 2). This method of preparation thus results in the formation of microparticles with a very large surface area.

Microparticles produced by this present invention have a rough pitted external surface, appear to be soft but may be hardened by cross-linking and will form continuous films, whereas microparticles produced by the prior art using aqueous ethanol have an almost smooth external surface, appear to be firmer and do not form continuous films.

Proteins for forming microparticles. The proteins are cereal prolamin proteins, and more particularly (but not exclusively), kafirin, gluten, hordein or zein or mixtures thereof. Typically, the protein is kafirin. Proteins are used to make microparticles since they are natural, have diverse properties, which can be modified, and are degradable both in vitro and in vivo to amino acids and small peptides. They are therefore suitable for human and animal consumption and for pharmaceutical administration. Hydrophobic proteins have limited solubility in water but are soluble in organic solvents, aqueous mixtures of organic solvents, binary solvents and solvents with extreme pHs, such as acids or bases. Kafirin is the preferred prolamin protein since it is more hydrophobic than other prolamins such as wheat gliadin and maize zein, and is also more crosslinked than zein, resulting in better functional properties.

The protein may be a protein isolate or may be extracted from a co-product material, such as brewers spent grain, distiller's dry grain with solubles or other co-products of alcohol production from cereals.

Acids used to make the microparticles. The protein is dissolved in an appropriate organic acid. The protein is usually considered soluble if 0.5% (w/v) of the protein dissolves in a solvent to form a clear solution at ambient temperature (20-25° C.) (Shukla, R. and Cheryan, M. (2001) Zein: The Industrial Protein From Corn, Industrial Crops and Products 13:171-192). Examples of organic acids which can be used to dissolve the proteins are acetic acid, lactic acid, and propionic acid. The use of these acids confers the advantage of food compatibility to the microparticles. In addition, the microparticles formed in this way are microbially stable and no additional preservatives are needed. The preferred acid in the process of this invention is acetic acid.

Powder formation. The microparticles can be separated from the dilute organic acid solution in which they are formed and washed with an aqueous solution. The aqueous solution is then removed and the microparticles dried to a powder. The method of separation can be, for example, filtration or centrifugation. The method of drying can include lyophilization, flash drying, spray drying, fluid bed drying or any other suitable drying method. The methods of separation and drying will typically be dependant on the protein used. The powder can be stored and handled without refrigeration or other special handling techniques. Re-hydration can be achieved by adding the powder to an dilute organic acid solution with agitation sufficient to re-suspend the particles. The amount of dilute organic acid solution used for reconstitution is dependant on the concentration of the final product required and the use for which it is required.

Figure 3:
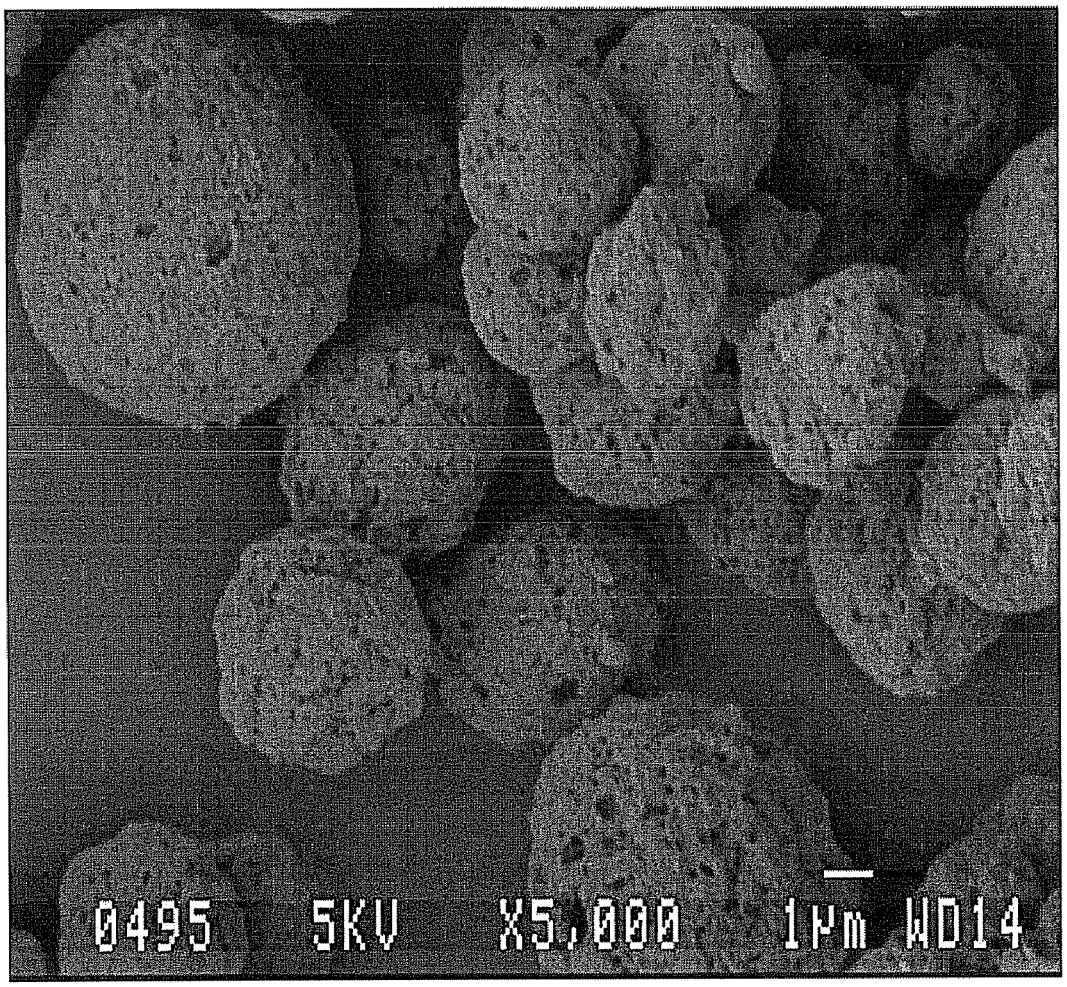
FIG. 3 shows a Scanning Electron Micrograph of freeze-dried kafirin microparticles produced according to the process of the present invention.

Microparticles which have been dried retain their structure. They are spherical or irregular in shape with a rough pitted surface, as shown by Scanning Electron Microscopy (FIG. 3).

Figure 4:
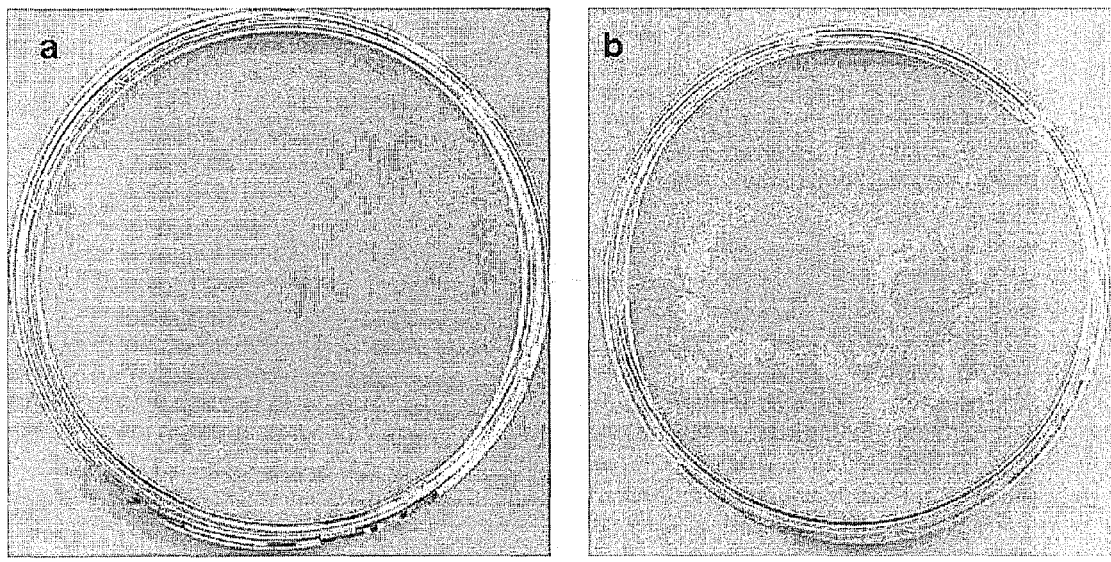
FIG. 4 shows: (a): a 2% kafirin microparticle film cast from 21.6% acetic acid, the film being approximately 15 microns thick, flexible, colourless, clear and transparent with a smooth surface; and (b): a 2% kafirin film cast from glacial acetic acid, the film being approximately 30 microns thick, flexible, almost colourless, clear, not completely transparent with a rough surface.

Film and coating formation. When the protein microparticles are to be used to form a free-standing film, the dilute organic acid suspension of the microparticles can be cast directly onto a casting surface. The liquid phase is then removed by drying, either with or without the application of heat. A complete (as opposed to fragmented, cracked or with holes) film is produced of variable thickness, depending on the concentration of protein used to make the microparticles (FIG. 4a). The film will typically have a thickness of 10-30 microns. The film may be used as a packaging material, such as for foodstuffs, food ingredients and pharmaceuticals for veterinary or human use. The film may also be used as an interleaving material, such as for separating portions of the same food product, for example pizza, or between different components in the same food product, such as the fruit filling and pastry in a pie to prevent moisture transfer. The film may be clear or cloudy.

When a coating is required on a substrate, the aqueous suspension of the microparticles is used to cover a surface of the substrate and the aqueous phase is then allowed to evaporate, forming a coating on the substrate surface. The substrate may be that of an edible foodstuff or food ingredient, which is sensitive to oxidation or moisture loss, such as a fruit, nut, spice or vegetable, either whole or minimally processed or processed or an animal or fish feed product. Other suitable products could also be coated, such as a flower, pharmaceutical compound, enzymes, hormones, tablet compositions, or other pharmaceutical, biological or medical products, nutrients, nutraceuticals, probiotics, prebiotics and the like, or combinations thereof.

It is important that the suspension of protein microparticles is diluted as set out in relation to the second and third processes of the invention, so as to produce films and coatings which are complete. This distinguishes the films and coatings from those made by prior art processes, using ethanol or different proportions of protein:solvent:water, which may not be complete. The films prepared according to the invention may also be clear or cloudy, transparent or translucent.

The dispersion of protein microparticles can be co-formulated with various additives, such as plasticizers, which improve the functional properties of films and coatings made from the microparticle dispersion. Films produced from protein microparticles are complete and can be made thinner than other films, such as from 10 μm to 30 μm, and preferably about 15 μm. The films may also have some superior functional properties to films produced by ethanolic solutions of proteins, such as water barrier properties and being clear, transparent or translucent (other cast films are often fragmented and opaque).

Encapsulation within matrices. When the protein microparticles to be formed are to be used to encapsulate a compound, the compound can be incorporated into the aqueous solution, organic acid or protein solution, or a combination thereof, prior to the formation of the microparticles. When the resulting solutions are mixed with agitation, microparticles are formed containing the compound which is to be encapsulated.

Another way to effect encapsulation of a compound into the microparticles is by mixing the previously dried microparticles of the invention with a substance in solution or suspension in which the microparticles are not soluble. On evaporation of such solvent the compound remains encapsulated within the microparticles.

Microparticle modification. The properties of the microparticles can be modified for a given application, for example by use of either chemical, enzymatic or physical means to change the starting protein prior to or during microparticle formation, or after formation of the microparticles, matrices or after or during forming films or coatings from the microparticles. Such modifications can produce microparticles, matrices, scaffolds, films or coatings with improved properties, such as altered thermal stability, shear stability or resistance to proteases. Films or coatings made by such modifications would also have improved functional properties including altered tensile and barrier properties, improved resistance to proteases and delayed biodegradation. Specific examples of protein modifications are crosslinking with tannins, using trans glutaminase enzymes and heating.

The present invention is further described by the following examples. Such examples, however, are not to be construed as limiting in any way either the spirit or scope of the invention.

EXAMPLES

Example 1

Formation of Kafirin Microparticles

A composition according to one embodiment of the invention was made by admixing the following (all percentages are given on a weight basis): a plasticizer (10%), glacial acetic acid (66%) and kafirin (24%), and the kafirin was dissolved in the acid. Distilled water was then added with stirring, and microparticles were formed. The concentration of protein was 2%, plasticizer 40% in relation to the protein content and an acid concentration of 5.4%.

The microparticles were prepared by weighing kafirin (1.8 g-88.63% protein) into a 125 ml Erlenmeyer flask. Plasticizer (0.66 g 1:1:1 lactic acid, polyethylene glycol (400), glycerol-40% in relation to protein) was mixed with glacial acetic acid (4.34 g) before adding to the kafirin with gentle stirring. The temperature was slowly raised to 30° C. to ensure full solvation. The protein solution was then left overnight (16 h) at room temperature to relax the protein. After this period distilled water was added slowly over a period of 5 min with stirring to a total weight of 80 g. On addition of the water the microparticles formed, appearing as a stable, white colloidal suspension. The particle size was from 1-10 microns, with the majority of microparticles measuring 3-4 microns. There was no apparent increase in particle size with storage at 8° C. over a period of 6 months. During this period, there was no microbial growth without any added antimicrobial agents. When viewed by Scanning Electron Microscopy, microparticles appeared as spheres with extensively pitted surfaces (FIG. 2). Internal structure determined by Transmission Electron Microscopy revealed internal vacuoles of varying size with smooth walls. These results show that microparticles prepared by the process of the present invention have very large internal surface areas.

Example 2

Formation of Zein Microparticles Using Either Acetic Acid, Lactic Acid or Propionic Acid A composition was made by admixing the following (all percentages are given on a weight basis): a plasticizer (9.5%), glacial acetic acid (62%) (or lactic acid or propionic acid) and commercial zein (ZPP Gold, Zein Protein Products, Marina, Calif.) (29.6%), and the zein was dissolved in the acid. Distilled water was then added with stirring, and microparticles were formed. The concentration of protein was 10%, plasticizer 40% in relation to the protein content and an acid concentration of 21.6%. To reduce the protein content further to 2%, 21.6% acetic acid was added.

The microparticles were prepared by weighing zein (4 g-100% protein) into a 125 ml Erlenmeyer flask. Plasticizer (1.32 g 1:1:1 lactic acid, polyethylene glycol (400), glycerol-40% in relation to protein) was mixed with glacial acetic acid (8.64 g) before adding to the zein with gentle stirring. The temperature was slowly raised to 30° C. to ensure full solvation. The protein solution was then left overnight (16 h) at room temperature to relax the protein. After this period distilled water was slowly over a period of 5 min with stirring to a total weight of 40 g, 10% zein, 21.6% acetic acid. On addition of the water the microparticles formed, appearing as a stable, white colloidal suspension. To reduce the protein concentration further, 21.6% acetic acid was used for dilution.

Example 3

Formation of a Coating Made with Kafirin Microparticles and Crosslinked by Heating in Order to Protect the Coated Material e.g. Methionine, a Limiting Amino Acid, from the Conditions in the Rumen of Multi-Gastric Animals Microparticles of the invention were used to make a dried powder. This powder prepared as described above in the section, 'powder formation' was mixed with a dry substance, in this case, the amino acid, methionine at a ratio of 1:1. The powder mixture was then mixed with glacial acetic acid (1:2) to form a paste with the aim of fusing together the microparticles around the substance, e.g. methionine and forming a continuous coating. The paste was then either dried directly on a flat surface or first underwent a simple extrusion procedure without exposure to heat or excessive pressure. The coated material was then heat treated in a force draught oven at 60-70° C. overnight. The microparticle coated methionine preparations were then subjected to dissolution and simulated pepsin digestion assays to determine methionine release characteristics.

Incubation conditions for the dissolution test simulated the conditions in the cow rumen with a pH of approximately 5.5 at 39° C. There was not a burst release of kafirin microparticle coated methionine. Instead after 8 h approximately 80% of the methionine was released from the glacial acetic acid fused microparticle coating compared with uncoated methionine, which was completely dissolved in less than 1 h under these conditions. Release of methionine appeared to be by diffusion through pores within the kafirin microparticle coating.

Thus, by coating the methionine or any other suitable compound with a microparticle coating, a delayed release of such compound is effected. This allows the compound to bypass the rumen and be absorbed in the intestine of the animal as desired.

Example 4

Formation of a Free-Standing Film Made with Kafirin Microparticles

In another embodiment, microparticles of the invention were used to make a free-standing film. A microparticle suspension prepared as described above in Example 1 (4 g-2% protein, 5.4% acetic acid per film) was weighed into plastic centrifuge tubes. The suspensions were centrifuged at 4000 g for 5 min. The supernatants were decanted off and replaced with an equal weight of 21.6% acetic acid. The protein suspensions were then left overnight at room temperature. Plasticizer (32 mg per film, mixed 1:1:1 lactic acid, polyethylene glycol (400), glycerol-40% in relation to protein) was added to the protein suspension. The suspension was then cast into clean, dry flat plastic containers. The containers were placed on a level surface in an oven (not forced draught) at 50° C. and dried for 4 hours. Films were gently peeled from the casting containers. Tensile and water barrier properties of the free standing films were then determined.

Free-standing films made from kafirin microparticles prepared by the method described herein have significantly lower water vapour permeability than films made with the same percentage kafirin using conventional film casting techniques. Tensile properties of kafirin microparticle films were similar to those cast using conventional film casting techniques.

Kafirin microparticle films were much thinner (approximately 15 microns) (FIG. 4a) than kafirin films (30 microns) of the same protein concentration cast using conventional film casting techniques (FIG. 4b). It is to be appreciated that the thickness of the free-standing microparticle films can be varied to obtain different properties. Similarly, the exact composition of the films can be varied, to impart different properties to the resultant films.

In addition the films were clear, colourless and transparent.

Example 5

Figure 5:
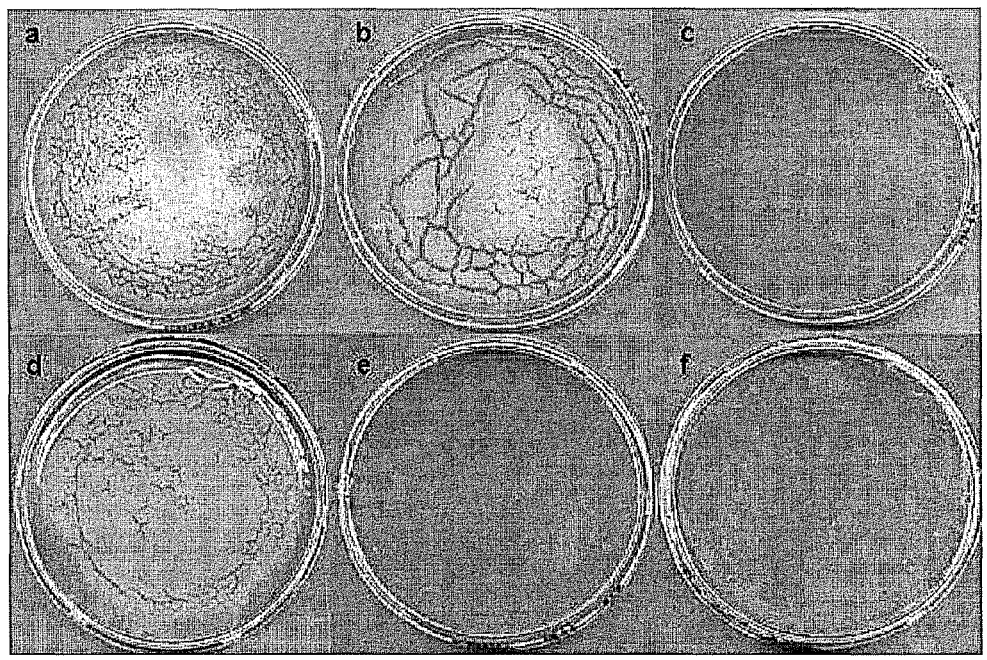
FIG. 5 shows the effect of kafirin microparticles made with different organic acids with increasing acid concentration on film formation, a-c acetic acid, 5.4%, 10.8%, 21.6%, d-f propionic acid, 5.4%, 10.8%, 21.6%, respectively. a and b show that complete, clear films cannot be formed at either 5.4% or 10.8% acetic acid, respectively. The films are opaque, fragmented and rough on the surface. In contrast, at 21.6% acetic acid a complete, colourless, clear, transparent and smooth film is formed (c). d shows that with 5.4% propionic acid a complete film cannot be formed. The film is opaque and fragmented with a rough surface but less so than in a and b where acetic acid is used at 5.4% and 10.8% respectively. e and f show that at 10.8% and 21.6% propionic acid, respectively, a complete, colourless, clear, transparent and smooth film is formed.

Formation of a Free-Standing Film Made with Kafirin Microparticles, Acid-Propionic Acid Microparticles, of the invention were used to make a free-standing film using an alternative organic acid e.g. propionic acid. A microparticle suspension prepared as described above in Example 1 (4 g-2% protein, 5.4% propionic acid per film) was weighed into plastic centrifuge tubes. The suspensions were centrifuged at 4000 g for 5 min. The supernatants were decanted off and replaced with an equal weight of 10.8% propionic acid. The protein suspensions were then left overnight at room temperature. Plasticizer (32 mg per film, mixed 1:1:1 lactic acid, polyethylene glycol (400), glycerol-40% in relation to protein) was added to the protein suspension. The suspension was then cast into clean, dry flat plastic containers. The containers were placed on a level surface in an oven (not forced draught) at 50° C. and dried for 4 hours. Films were gently peeled from the casting containers (FIG. 5e). Tensile, water barrier properties and protein digestibility of the free standing films were then determined (Table 1).

Kafirin microparticle films cast from propionic acid were similar in thickness (approximately 15 microns) (FIG. 5e) and appearance (clear, colourless and transparent) to kafirin microparticle films cast from acetic acid (FIG. 5c) and thinner than kafirin films (30 microns) of the same protein concentration cast using conventional film casting techniques (FIG. 4b).

TABLE 1

Functional properties of free-standing kafirin films

| Functional Properties | 2% Kafirin microparticle film (acetic acid) | 2% Kafirin microparticle film (propionic acid) | 2% Kafirin film cast from glacial acetic acid |
|---|---|---|---|
| Thickness (μm) | 14.0 (3.0)* | 14.0 (5.0) | 30.0 (3.4) |
| Water Vapour Permeability (gmm/m²hkPa) | 0.22 (0.05) | 0.36 (0.11) | 0.50 (0.11) |
| Stress at break (N/mm²) | 3.72 (4.87) | 2.39 (4.13) | 5.39 (2.07) |
| Elongation (%) | 2.53 (3.37) | 1.15 (1.81) | 2.99 (1.79) |
| Protein digestion (%) | 65.7 (2.5) | 69.9 (6.7) | 89.0 (1.3) |

*FIGURES in parentheses indicate standard deviations

Example 6

Encapsulation of Dietary Antioxidants within Kafirin Microparticles for Monogastric Animals Including Humans Microparticles of the invention were used to make a dried powder. This powder prepared as described above in the section, 'powder formation' was mixed with a compound in solution, in this case, the polyphenolic antioxidants catechin or sorghum condensed tannins dissolved in 70% acetone, a solvent in which the microparticles are not soluble. On evaporation of such solvent the compound remained encapsulated within the microparticles. The level of encapsulation was 20% polyphenol in relation to protein. The examples used do not exclude the use of other substances or different solvents for those substances. The microparticle encapsulated antioxidants were then subjected to dissolution and simulated digestion to determine the release profiles of the encapsulated antioxidants. Incubation conditions simulated those of the human digestive system, that is 2 h at 37° C. with pepsin at pH 2.0 followed by a further 2 h incubation at the same temperature with trypsin/chymotrypsin at pH 7.6.

After an initial small burst release, over a further period of four hours, catechin and condensed tannin encapsulated kafirin microparticles showed virtually no protein digestion but released approximately 70% and 50%, respectively, of their total antioxidant activity. This demonstrates that encapsulation of polyphenolic antioxidants within kafirin microparticles would allow controlled release of the encapsulated compound in the human stomach and gastrointestinal tract. It is to be appreciated that loadings of active compound could be varied in order to obtain different dosage levels. Similarly, the kafirin microparticles with the encapsulated compound may undergo further treatment, for example, by heat, in order to modify the release profile of the encapsulated compound.

Example 7

Extraction of Kafirin from Sorghum Brewers Spent Grain (Co-Product) and the Direct Preparation of Kafirin Microparticles Sorghum brewers spent grain (moisture content 75%) was presoaked for 16 h in a 0.5% aqueous solution of sodium metabisulphite at a solid to solvent ratio of 1:5. The sodium metabisulphite was removed and the brewers spent grain was extracted with glacial acetic acid at a solid to solvent ratio of 1:5 for 48 h at ambient temperature. The extract (protein solution) was then separated from the solid material. The solid material was washed with a further equal amount of glacial acetic acid and the two extracts combined. Microparticles were then made by the slow addition of water to the glacial acetic acid extract (protein solution) with constant agitation. The ratio of extract (protein solution) to water added was 1:3 (the ratio of protein to acid to water is approximately 2 parts protein, 25 parts acetic acid and 73 parts of water, depending on the original protein content of the brewers spent grain). The resulting microparticles were then separated from the liquid and washed with water to remove any residual acid before drying. The dried microparticles made by this method had a kafirin purity of 95% and could then be used in any of the applications described in this document.

Example 8

Figure 6:
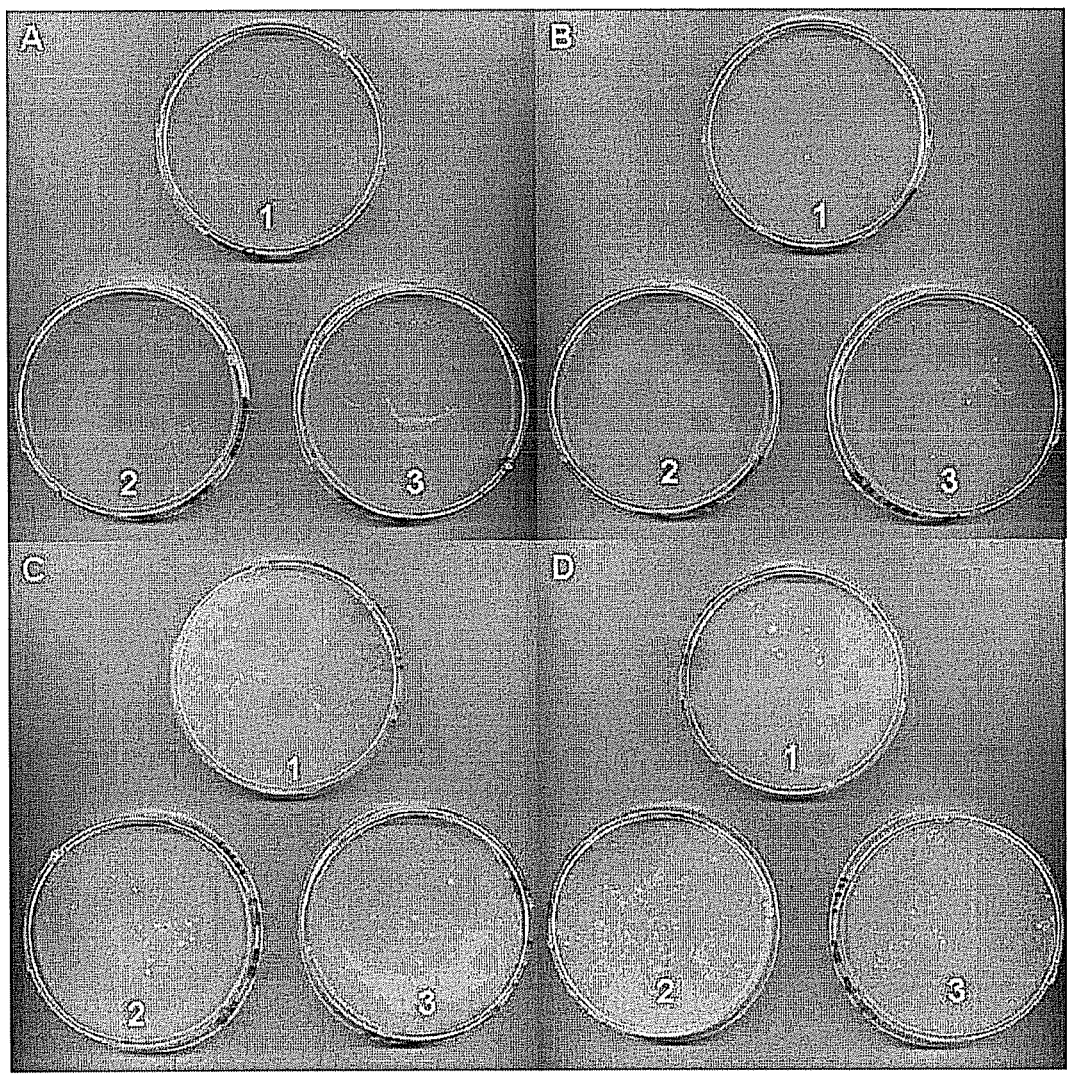
FIG. 6 shows films and coatings made from microparticles made directly from an extract of sorghum brewers spent grains. A-20% acetic acid, B-10% acetic acid, C-2% acetic acid, D-1% acetic acid; 1-2% kafirin, 2-1% kafirin, 3-0.5% kafirin. Note all the films are complete.

Direct Preparation of Kafirin Microparticle Films or Coatings from an Extract of Sorghum Brewers Spent Grain Microparticles made from sorghum brewers spent grain as described in example 7 were used to make free-standing films and coatings. Instead of washing and drying the microparticles, the suspension of microparticles can be taken directly and dried into a film or coating. In addition, if desired, the acid or protein concentration can be manipulated as described in Example 4 in order to produce films and coatings of different thicknesses and with different functional properties (FIG. 6). Films made in this way were slightly thicker than those made from isolated kafirin, being approximately 25 microns when 2% kafirin was used and 15 microns when 1% kafirin was used. Lower protein concentrations resulted in coatings which could not be separated from the casting surface.

Films made from this and other co-products were usually slightly cloudy but still complete. The cloudiness is probably due to the impurities co-extracted with the kafirin. Making microparticles from pure kafirin and then using these microparticles to make films we get clear, transparent films which are complete.

Example 9

Figure 7:
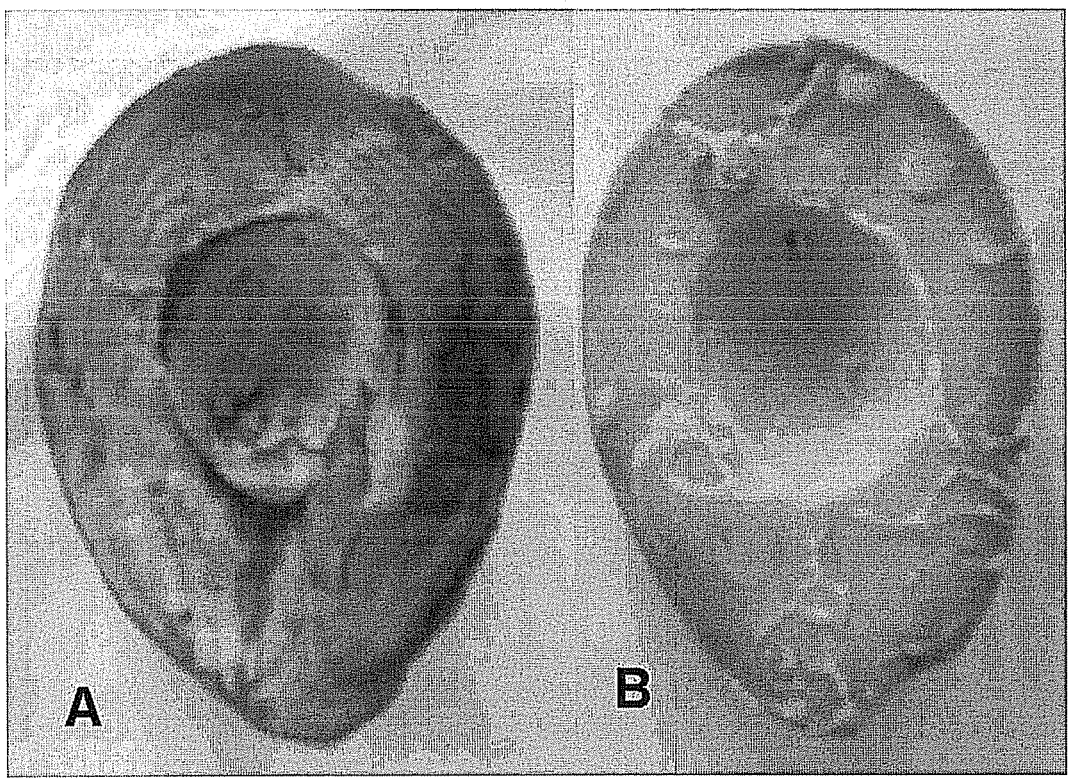
FIG. 7 shows minimally processed avocados stored for 5 days at 4° C. A: uncoated avocados, B: avocados coated with a kafirin microparticle coating formulation according to the invention.

Use of a Kafirin Microparticle Coating Formulation to Extend the Shelf Life of Minimally Processed Avocados Microparticles made from sorghum brewers spent grain as described in Example 7 were used to make a coating formulation which was applied to cut halves of eat-ripe avocados to extend the fruits' shelf life. Class 1 export avocados (Persea americana Mill) variety 'Hass' were used in the experiment. The avocados were stored at 4° C. 5 days prior to the start of the experiment. The avocados were then ripened at 22° C. until eat-ripe. They were peeled and halved by hand before dipping in the coating formulation solution. The coating formulation solution consisted of 2% kafirin protein in 2% (v/v) acetic acid with 1:1:1 plasticiser of propylene glycol, lactic acid and glycerol (40% w/w with respect to protein). Uncoated avocado halves were used as controls. After the coating had dried, the fruit halves were packaged in plastic tubs, which were closed with plastic lids, and stored at 4° C. for 5 days. After the period of 5 days, the microparticle-coated avocados showed no evidence of browning, whereas the control avocados showed extensive browning (FIG. 7).

While the invention has been described in detail with respect to specific embodiments thereof, it will be appreciated by those skilled in the art that various alterations, modifications and other changes may be made to the invention without departing from the spirit and scope thereof.

What is claimed is:

1. A process for making protein microparticles, the process including the steps of:
   (a) dissolving dry cereal prolamin protein in a concentrated organic acid with agitation and in the absence of an alcohol; and
   (b) diluting the solution containing the protein with an aqueous solution, thereby forming protein microparticles having vacuoles.

2. A process according to claim 1, wherein the cereal prolamin protein is selected from the group consisting of gluten, hordein, zein, kafirin, and combinations thereof 3. A process according to claim 1, wherein the organic acid is selected from the group consisting of propionic acid, lactic acid, acetic acid, and combinations thereof 4. A process according to claim 1, which is carried out in the absence of ethanol.

5. A process according to claim 1, wherein in step (a) the protein solution is saturated or highly concentrated.

6. A process according to claim 1, wherein the agitation is provided by stirring, shaking, homogenization, or bubbling gas through the solution.

7. A process according to claim 1, wherein the protein is crosslinked with tannins or enzymes and/or heat treated before or after step (a).

8. A process according to claim 1, which further includes a step of removing the organic acid from the diluted solution.

9. A process according to claim 1, which further includes a drying step.

10. A process according to claim 1, which further includes a step of forming a powder, film, coating, matrix, or scaffold from the diluted solution.

11. A process according to claim 1, wherein the solution in step (a) is allowed to stand for 8 to 24 hours.

12. A process according to claim 1, wherein in step (b) the solution containing the protein is diluted with water to a final concentration of about 2 parts by weight of the protein to about 2 to about 30 parts by weight of the organic acid to about 96 to about 68 parts by weight of water.

13. A process according to claim 1, wherein an additive, selected from the group consisting of a plasticizer, colouring agent, flavouring agent, preservative, trace mineral, nutrient, enzyme, hormone, nutraceutical, probiotic, prebiotic, pharmaceutical, and combinations thereof, is added to the solution of step (a) or (b) and is incorporated into or encapsulated by the protein microparticles.

14. A process according to claim 13, wherein the additive is a plasticizer selected from the group consisting of glycerol, polyethylene glycol, polypropylene glycol, lactic acid, dibutyl tartrate, monoglycerides, palmitic acid, stearic acid, triethylene glycerol, sorbitol, and combinations thereof 15. A process according to claim 14, wherein the plasticizer is present in an amount of from about 0.2 to about 0.6 parts by weight to about 1 part by weight of the protein.

* * * * *